US009737458B1

(12) United States Patent
Olivares et al.

(10) Patent No.: US 9,737,458 B1
(45) Date of Patent: Aug. 22, 2017

(54) PROSTATE MASSAGER

(71) Applicant: Shenzhen Aigan Technology Co. Ltd., Shenzhen (CN)

(72) Inventors: Eddy Olivares, Guangzhou (CN); Dan Liu, Guangzhou (CN)

( * ) Notice: Subject to any disclaimer, the term of this patent is extended or adjusted under 35 U.S.C. 154(b) by 0 days.

(21) Appl. No.: 15/464,555

(22) Filed: Mar. 21, 2017

(51) Int. Cl.

| | |
|---|---|
| ***A61F 5/00*** | (2006.01) |
| ***A61H 23/02*** | (2006.01) |
| ***A61H 21/00*** | (2006.01) |

(52) U.S. Cl.
CPC ............. *A61H 23/02* (2013.01); *A61H 21/00* (2013.01); *A61H 2201/5023* (2013.01)

(58) Field of Classification Search
CPC ........ A61H 23/02; A61H 19/00; A61H 19/30; A61H 19/34; A61H 19/40; A61H 19/44
USPC ......................................... 600/38–41; 601/46
See application file for complete search history.

(56) References Cited

U.S. PATENT DOCUMENTS

| | | | | |
|---|---|---|---|---|
| 2005/0273024 A1* | 12/2005 | Nan | ........................ | A61H 19/44 601/71 |
| 2014/0228628 A1* | 8/2014 | De Alva | ................ | A61H 19/44 600/38 |
| 2014/0350333 A1* | 11/2014 | Stout | ...................... | A61H 19/44 600/38 |
| 2016/0045392 A1* | 2/2016 | Massey | .................. | A61H 23/02 601/46 |
| 2016/0120737 A1* | 5/2016 | Sedic | ..................... | A61H 19/34 601/46 |

* cited by examiner

*Primary Examiner* — John Lacyk
(74) *Attorney, Agent, or Firm* — Steinberg Intellectual Property Law LLC; Gloria M. Steinberg, Esq.

(57) ABSTRACT

Disclosed is a prostate massager that includes a first section connected to a second section. The first section can bend relative to the second section at various angles to optimize prostate stimulation. Each of the first section and the second section includes a vibrating unit that can facilitate massaging. The vibrating unit can be controlled via a control switch that is operatively connected to a printed circuit board. The printed circuit board can include a network interface for connecting the massager to an external user device to remotely control the massager.

14 Claims, 3 Drawing Sheets

PROSTATE MASSAGER

FIELD OF THE INVENTION

The present invention generally relates to sexual stimulation devices and adult toys. More particularly, the present invention is directed to a prostate massager.

BACKGROUND OF THE INVENTION

Prostate massage is often used for sexual stimulation. The prostate is sometimes referred to as the "male G-spot." Many couples utilize a finger for anal penetration and prostate stimulation to enhance the man's orgasm. The main problem in using the finger, however, is that it may be too short to reach the prostate gland. Thus, a prostate massager can be used to more effectively massage the prostate gland. The shape of a prostate massager is similar to a finger, since prostate massages are traditionally given digitally. Existing prostate massage equipment ranges from dildos to butt plugs and G-spot vibrators. These devices are configured to be inserted into the rectum through the anus and are intended to stimulate the prostate by massaging or vibrating.

While various prostate massage equipment exists in the art, many are not commonly intended to stimulate the prostate in an optimal manner. For example, most butt plugs are generally inserted and left in place without means to accommodate various body types and means to stimulate the user. In this regard, users must try different positions to ensure that the massager is positioned properly and stays in the desired area or flex their muscles to move the massager for prostate stimulation. Thus, improved massagers that are designed to provide a more direct and thorough massage of the prostate gland is needed. In this regard, the invention described herein addresses these problems.

SUMMARY OF THE INVENTION

In view of the disadvantages inherent in the known types of prostate massage equipment now present in the prior art, the present invention provides an improved prostate massager.

The following discloses a simplified summary of the specification in order to provide a basic understanding of some aspects of the specification. This summary is not an extensive overview of the specification. It is intended to neither identify key or critical elements of the specification nor delineate the scope of the specification. Its sole purpose is to disclose some concepts of the specification in a simplified form as to prelude to the more detailed description that is disclosed later.

Some embodiments include a prostate massager comprising a first section that is substantially orthogonal to a second section, wherein the first section is configured to bend relative to the second section so as to adjust the shape and the angle of the massager. In some embodiments, the first section is connected to the second section via a metal arm that can be bent at various angles and directions when manipulated by a user.

In some embodiments, each or one of the first section and the second section comprises a vibrating unit embedded therein. The vibrating units are operatively connected to a power source (e.g., a rechargeable battery) and a printed circuit board (PCB), which is connected to a controller switch for operating the vibrating units. In some embodiments, the vibrating units can be operated separately or concurrently.

In some embodiments, the PCB comprises a network interface for communicating with an external user device such as a smart phone, personal digital assistant (PDA), tablet computer, a laptop, a desktop, or other types of processing systems. In some embodiments, the external user device comprises a downloadable or non-downloadable application for operating the massager. In this way, the massager can be operated remotely.

It is, therefore, an objective of the present invention to provide a new and improved prostate massager that can be adjusted into various positions and angles to optimize prostate stimulation.

It is another objective of the present invention to provide a new and improved prostate massager that is anatomically shaped and that is ergonomic.

A final object of the present invention to provide a new and improved prostate massager that may be readily fabricated from materials that permit relative economy and commensurate with durability.

In the light of the foregoing, these and other objectives are accomplished in accordance with the principles of the present invention, wherein the novelty of the present invention will become apparent from the following detailed description and appended claims.

BRIEF DESCRIPTION OF THE DRAWINGS

The above and other objects and advantages of the present invention will be apparent upon consideration of the following detailed description, taken in conjunction with the accompanying exemplary drawings, in which like reference characters refer to like parts throughout, and in which.

DETAILED DESCRIPTION OF THE INVENTION

The present invention is directed towards a prostate massager. For purposes of clarity, and not by way of limitation, illustrative views of the present system and method are described with references made to the above-identified figures. Various modifications obvious to one skilled in the art are deemed to be within the spirit and scope of the present invention.

The word "exemplary" is used herein to mean serving as an example, instance, or illustration. Any aspect or design described herein as "exemplary" is not necessarily to be construed as preferred or advantageous over other aspects or designs. Rather, use of the word exemplary is intended to disclose concepts in a concrete fashion. As used in this application, the term "or" is intended to mean an inclusive "or" rather than an exclusive "or."

Additionally, the articles "a" and "an" as used in this application and the appended claims should generally be construed to mean "one or more" or "at least one" unless specified otherwise or clear from context to be directed to a singular form. Similarly, the terms "plurality" and "a plurality" as used herein includes, for example, "multiple" or "two or more." For example, "a plurality of items" includes two or more items.

Some embodiments may be used in conjunction with various devices and systems, for example, a personal computer (PC), a desktop computer, a mobile computer, a laptop, a tablet computer, a server computer, a handheld device, a personal digital assistant (PDA), a wireless communication device, a smart phone, a non-portable device, a wireless access point (AP), a wired or wireless router, a wired or wireless modem, a wired or wireless network, a local area network (LAN), a wireless LAN (WLAN), a metropolitan area network (MAN), a wireless MAN (WMAN), a wide area network (WAN), a wireless WAN (WWAN), a personal area network (PAN), a wireless PAN (WPAN), or networks operating in accordance with existing and/or future versions and/or derivatives of long term evolution (LTE), a device which incorporates a global positioning system (GPS) receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, or the like.

Some embodiments of the present invention may include one or more wired or wireless links, may utilize one or more components of wireless communication (e.g., Bluetooth®, Wi-Fi™), may utilize one or more methods or protocols of wireless communication, or the like. Some embodiments may utilize wired communication and/or wireless communication.

Figure 1:
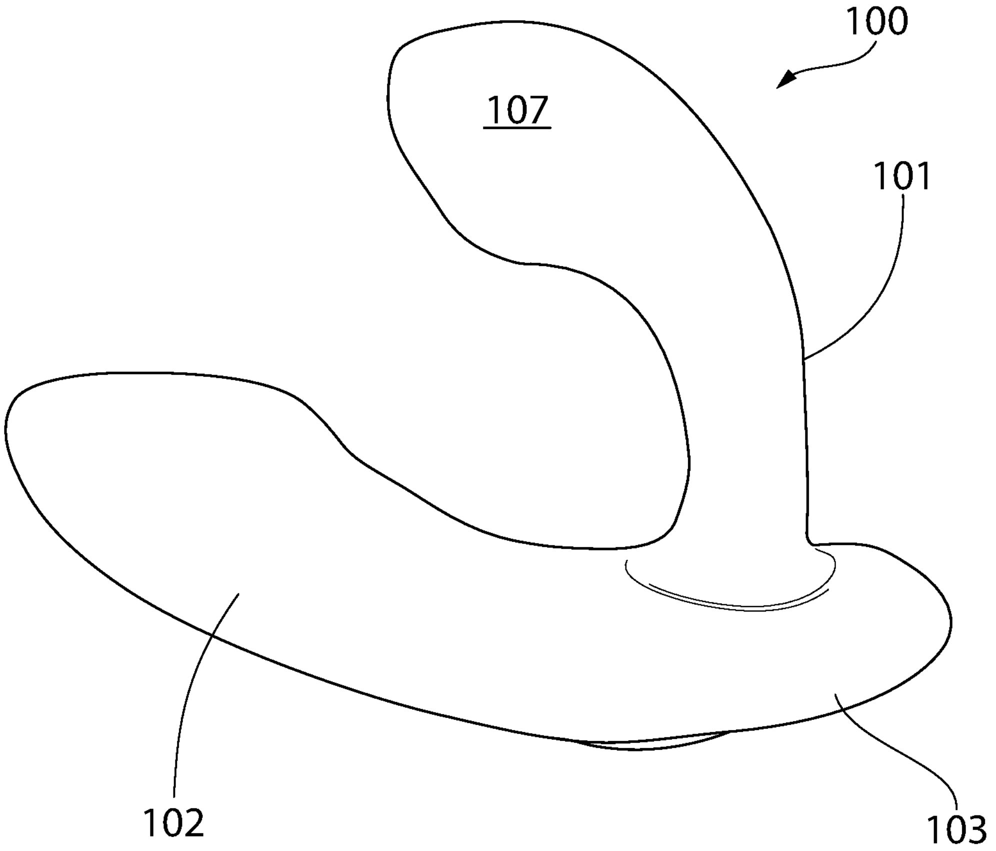
FIG. 1 depicts a side view of one embodiment of the present invention.
Figure 2:
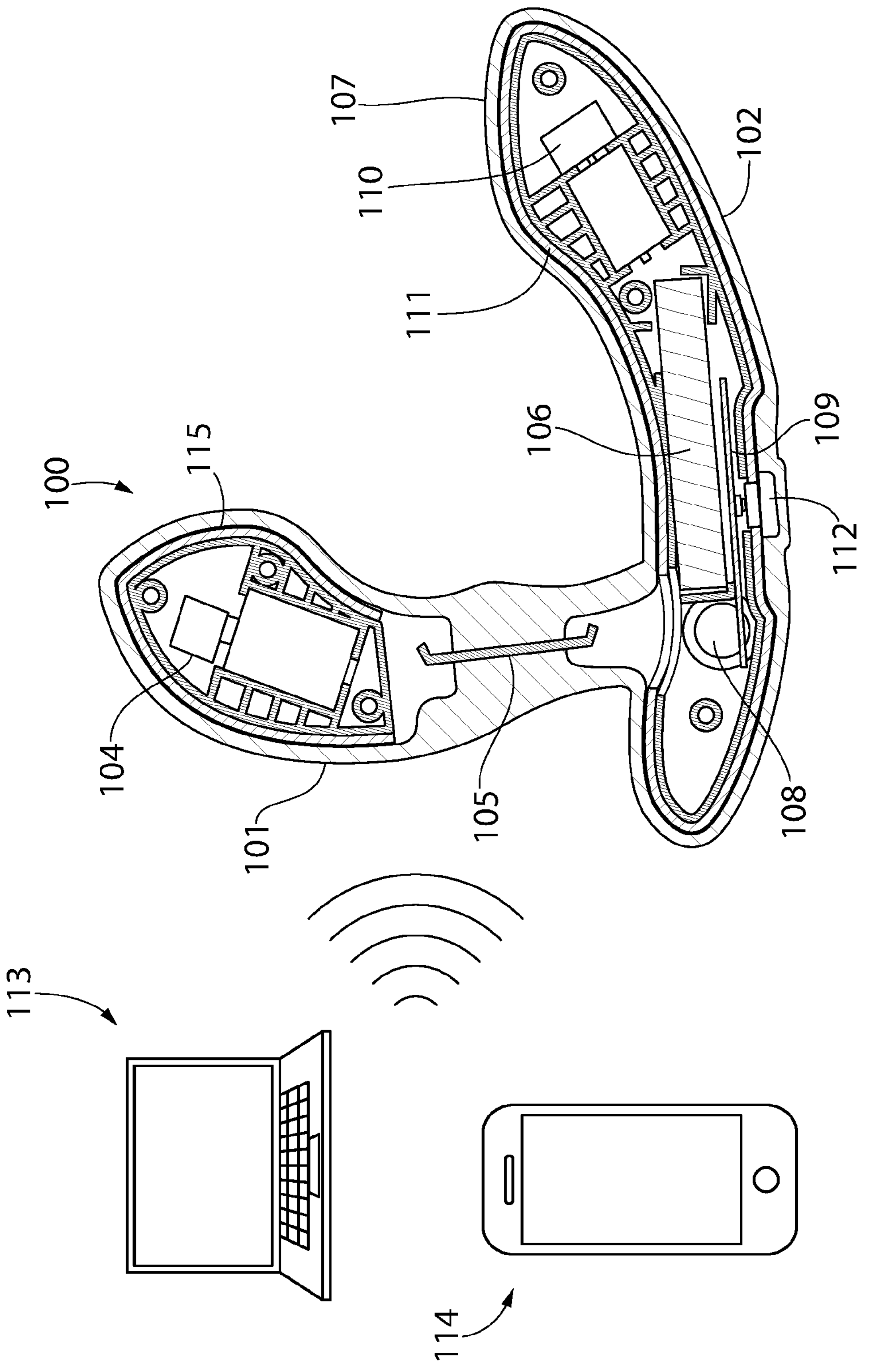
FIG. 2 depicts a cross-sectional view of an embodiment of the present invention.
Figure 3:
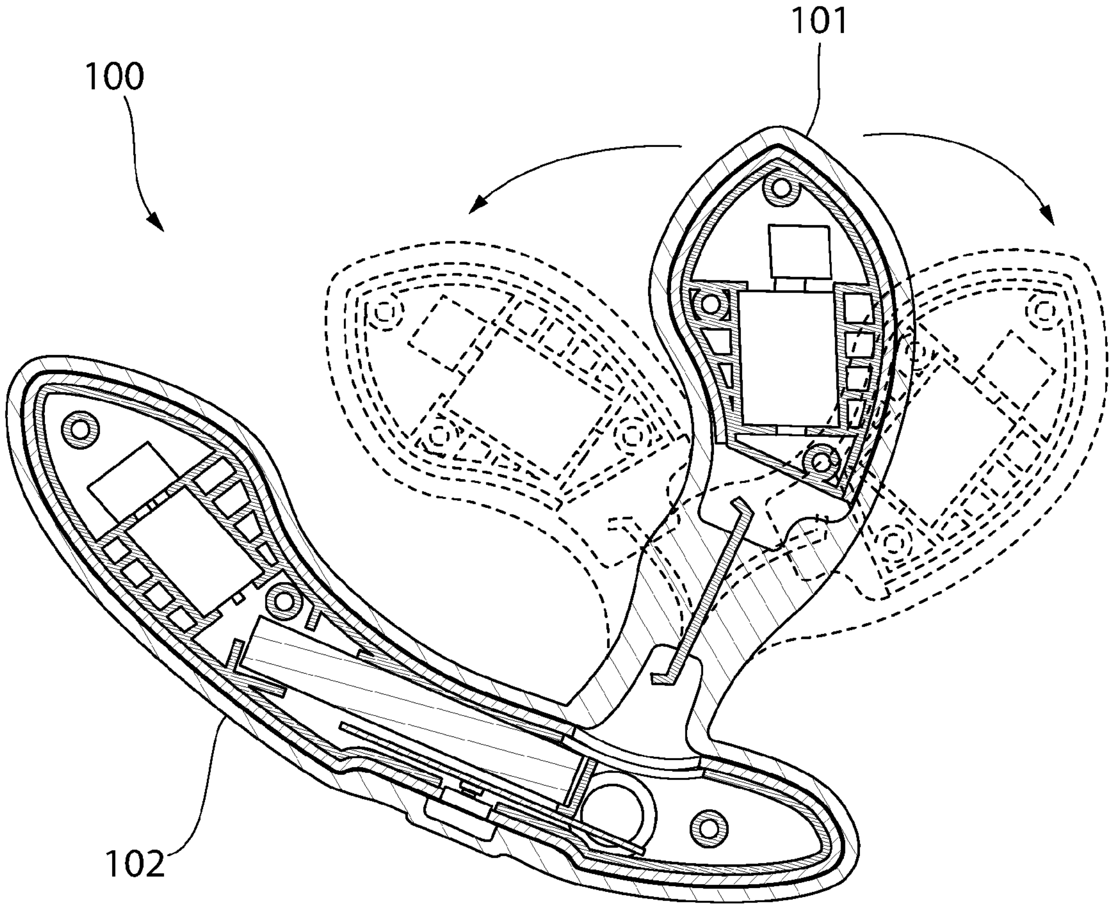
FIG. 3 shows a view of the present invention bent at multiple angles.

Referring now to FIGS. 1 through 3, there are shown various views of the prostate massager of the present invention. The prostate massager 100 comprises a first section 101 that is connected to a second section 102 at an elbow 103, forming a substantially L-shape or a V-shape when viewed from the top. In the illustrated embodiment, the elbow 103 can extend beyond the first section 101 so as to provide better handle or grip of the massager 100. In some embodiments, the elbow 103 does not extend beyond the first section 101.

Each of the first section 101 and the second section 102 is substantially phallus-shaped. In this regard, the diameter of the cross-section of each of the first section 101 and the second section 102 is not uniform over its length. In some embodiments, the first section 101 and the second section 102 comprise protrusions, ridges, bumps, depressions, or dimples. In some embodiments, the terminal ends or distal ends of the first section 101 and the second section 102 may be rounded or slightly tapered. Additionally, the first section 101 is of sufficient length to reach the prostate gland of a user. It is contemplated that the length of the second section 102 can vary slightly depending on embodiments as the second section 102 is designed for perineum stimulation.

The first section 101 comprises a first housing member 115 and the second section 102 comprises a second housing member 111, each having a defined interior volume for maintaining interior components therein. The first housing member 115 spans substantially half of the length of the first section 101 and is biased toward the terminal end or the distal end of the first section 101. The second housing member 111 spans substantially the entire length of the second section 102. In this regard, the first housing member 115 and the second housing member 111 are separated by a space and there is no rigid structure between the second housing member 111 and the first housing member 115.

The housing members 111, 115 can be composed of plastic or other rigid and durable materials. The exterior surface of the housing members 111, 115 comprises a silicone casing 107 or other types of casings that are composed of materials having a smooth and soft texture that has a skin-like feel. Preferably, the casing 107 is substantially seamless to facilitate the smoothness of the exterior surface and to mimic the feel of a human body part. Because the housing members are enclosed in a single casing, the massager 100 is unitary in structure.

The first housing member 115 is connected to the second housing member 111 via at least one metal arm 105 that is configured to bend in multiple directions and in multiple angles when manipulated by a user. The metal arm 105 spans between the substantial midpoint of the first section 101 and the elbow 103, or between the first housing member 115 and the second housing member 111. The metal arm 105 can be partially embedded within the first housing member 115 and the second housing member 111.

The metal arm 105 is configured bend to move the first section 101 so as to change the position of the first section 101 relative to the second section 102. Once bent into the desired position, the metal arm 105, and hence the first section 101, stays in the desired position until manipulated by a user later into a second desired position, and so on.

In the illustrated embodiments, the metal arm 105 can be used to position the first section 101 at a starting position, wherein the first section 101 is substantially perpendicular to the second section 102 in the starting position. The metal arm 105 can also position the first section 101 at a second position, wherein the first section 101 is bent toward the second section 102 in the second position. The metal arm 105 can also position the first section 101 at a third position, wherein the first section 101 is bent away from the second section 102 in the third position. In this regard, moving the first section 101 changes the angle defined between the first section 101 and the second section 102 (i.e., an angle at or near the elbow 103).

It is contemplated that the first section 101 can also be bent so that the first section 101 and the second section 102 are in different planes, whereby the terminal end or the distal end of the first section 101 has an axis in a plane different from the plane of the terminal end or the distal end of the second section 102. The ability to manipulate the positioning of the first section 101 relative to the second section 102 and maintaining that position of the first section 101 enables the user to utilize the massager 100 in a truly hands-free manner while allowing the massager 100 to effectively reach the desired area on the user's body to stimulate the user's prostate.

In an exemplary embodiment, the metal arm 105 is composed of stainless steel and is approximately 1.5 mm in thickness. However, various type of tubing, sheets, strips, wire, and/or rods that are composed of different types of metal or other malleable materials in different thickness that can be bent into a desired position and then maintained at the desired position until subsequently manipulated by a user may be used, depending upon embodiments.

The first housing member 115 of the first section 101 further comprises a first vibrator unit 104 therein. The first vibrator unit 104 is configured to vibrate the first section 101 of the massager 100. The second housing member 111 of the second section 102 comprises a printed circuit board (PCB) 109 that is operatively connected to the first vibrator unit 104, a second vibrator unit 110, a power source (e.g., battery 106), and a control switch 112. The power source 106 preferably comprises a rechargeable battery that can be charged when connected to another power source (e.g., an electrical outlet) via a charging port 108. The second vibrator unit 110 is configured to vibrate the second section 102 of the massager 100. The first vibrator unit 104 and the second vibrator unit 110 can comprise the same type of vibrator units or different types of vibrator units, depending upon embodiments.

The control switch 112 comprises a button that can be operated as a power switch to turn on and turn off the massager 100. Additionally, the control switch 112 can be configured to change the vibration settings (e.g., speed, intensity, vibration pattern, etc.) for the first vibrator unit 104 and/or the second vibrator unit 110. More specifically, the control switch 112 can be depressed a preset number of times to change the vibration setting. For example, the control switch 112 can be depressed once for a slow speed, twice for a medium speed, and three times for a high speed. In some embodiments, the massager 100 comprises a control switch 112 for each of the vibrator units to enable a user to control the vibrator units separately.

The PCB 109 comprises an NFC or Bluetooth® interface so as to allow the massager 100 to communicate with one or more external user devices such as a handheld device 114, computer systems 113, or another system that comprises a processing unit that is operatively connected to a memory unit having a set of instructions stored thereon for operating the massager 100 such that when executed by the processor, the system is configured to establish a connection with the massager 100 to operate the same.

In some embodiments, the instructions result in an application, wherein the application comprises a web application, a mobile application, a website, a browser extension, a plug-in, or the like. It is contemplated that the application comprises a graphical user interface (GUI) for receiving user input and for operating the massager 100. In this way, the massager 100 can be operated remotely.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A prostate massager, comprising:

a first section connected to a second section at an elbow;

each of said first section and said second section comprising a vibrating unit that is operatively connected to a printed circuit board; and a bendable arm connecting said first section and said second section, wherein said arm is at least partially embedded within said first section and said second section, further wherein said arm is configured to bend in a first position to move said first section toward said second section and bend in a second position to move said first section away from said second section such that said first section is configured to remain in said first position or said second position until subsequently manipulated by a user.

2. The prostate massager of claim 1, further comprising a power source and a control switch operatively connected to said printed circuit board.

3. The prostate massager of claim 2, further comprising a charging port on said second section for recharging said power source.

4. The prostate massager of claim 1, further comprising:

a first housing member embedded within said first section, wherein said first housing member comprises a first vibrating unit; and a second housing member embedded within said second section, wherein said second housing member comprises a second vibrating unit.

5. The prostate massager of claim 4, wherein said first vibrating unit and said second vibrating unit are configured to vibrate concurrently.

6. A prostate massager, comprising:

a first housing member that is connected to a second housing member via an adjustable arm for movement between a starting position and a second position;

said arm at least partially embedded within said first housing member and said second housing member, wherein said first housing member is substantially perpendicular to said second housing member in said starting position, further wherein said first housing member is bent toward said second housing member in said second position, further wherein said first housing member remains in said second position until subsequently manipulated by a user.

7. The prostate massager of claim 6, wherein said first housing member comprises a vibrating unit;

said vibrating unit operatively connected to a control switch for operating said vibrating unit.

8. The prostate massager of claim 7, wherein said second housing member comprises a second vibrating unit;

said second vibrating unit operatively connected to said control switch for operating said second vibrating unit.

9. The prostate massager of claim 7, further comprising a printed circuit board operatively connected to said vibrating unit and said control switch.

10. The prostate massager of claim 9, wherein said printed circuit board comprises a network interface for establishing communication with an external user device, wherein said external user device is configured to remotely control said vibrating unit.

11. The prostate massager of claim 6, wherein said first housing member is bent away from said second housing member in a third position, further wherein said first housing member remains in said third position until subsequently manipulated by said user.

12. The prostate massager of claim 6, wherein said first housing member is bent relative to said second housing member such that said first housing member and said second housing member are in different planes.

13. The prostate massager of claim 6, wherein each of said first housing member is embedded within a first section and said second housing member is embedded within a second section, further wherein each of said first section and said second section are substantially phallus shaped.

14. The prostate massager of claim 6, wherein said first housing member and said second housing member are enclosed in a casing such that said first housing member and said second housing member are unitary in structure.

* * * * *